US011260104B2

(12) United States Patent
Jun et al.

(10) Patent No.: US 11,260,104 B2
(45) Date of Patent: Mar. 1, 2022

(54) CARRIER COMPOSITION FOR EYE DROPS AND PHARMACEUTICAL COMPOSITION INCLUDING THE SAME

(71) Applicant: HYUNDAIBIOSCIENCE Co., Ltd., Gimcheon-si (KR)

(72) Inventors: Young Joo Jun, Seoul (KR); Ji Hyun Kim, Seoul (KR); Byung Woo Yoo, Seoul (KR); Ji Young Choi, Seoul (KR)

(73) Assignee: HYUNDAIBIOSCIENCE Co., Ltd., Gimcheon-si (KR)

( * ) Notice: Subject to any disclaimer, the term of this patent is extended or adjusted under 35 U.S.C. 154(b) by 0 days.

(21) Appl. No.: 16/643,564

(22) PCT Filed: Dec. 27, 2019

(86) PCT No.: PCT/KR2019/018642
§ 371 (c)(1),
(2) Date: Mar. 1, 2020

(87) PCT Pub. No.: WO2020/139038
PCT Pub. Date: Jul. 2, 2020

(65) Prior Publication Data
US 2021/0213099 A1 Jul. 15, 2021

(30) Foreign Application Priority Data

Dec. 28, 2018 (KR) .......... 10-2018-0172598
Dec. 27, 2019 (KR) .......... 10-2019-0176553

(51) Int. Cl.
*A61K 9/00* (2006.01)
*A61K 38/17* (2006.01)
*A61P 27/02* (2006.01)
*A61P 37/06* (2006.01)
*A61K 9/06* (2006.01)
*A61K 9/50* (2006.01)
*A61K 31/196* (2006.01)
*A61K 31/407* (2006.01)
*A61K 31/573* (2006.01)
*A61K 31/575* (2006.01)

(52) U.S. Cl.
CPC .......... *A61K 38/1709* (2013.01); *A61K 9/06* (2013.01); *A61K 9/5042* (2013.01); *A61K 9/5073* (2013.01); *A61K 31/196* (2013.01); *A61K 31/407* (2013.01); *A61K 31/573* (2013.01); *A61K 31/575* (2013.01); *A61P 27/02* (2018.01); *A61P 37/06* (2018.01)

(58) Field of Classification Search
CPC .......... A61K 38/1709; A61K 9/5073; A61K 9/5042; A61K 9/06; A61K 31/196; A61K 31/407; A61K 31/575; A61K 31/573; A61P 37/06; A61P 27/02
See application file for complete search history.

(56) References Cited

U.S. PATENT DOCUMENTS

2014/0364392 A1* 12/2014 Ghosh .............. A61P 9/14
514/58

FOREIGN PATENT DOCUMENTS

| KR | 10-0775065 B | 11/2007 | |
|---|---|---|---|
| KR | 10-0938500 B | 1/2010 | |
| WO | 2015/164950 A1 | 11/2015 | |
| WO | WO-2015164950 A1 * | 11/2015 | .......... A61K 31/155 |

OTHER PUBLICATIONS

N. H. Shah, et al, Carboxymethylcellulose: Effect of Degree of Polymerization and Substitution on Tablet Disintegration and Dissolution, 70 J Pharm. Sci. 611 (Year: 1981).*
Gabriela Buhus, et al, Controlled Release of Water Soluble Antibiotics by Carboxymethylcellulose- and Gelatin-Based Hydrogels Crosslinked with Epichlorohydrin, 43 Cellulose Chem. Technol. 141 (Year: 2009).*
Mst. Sarmina Yeasmin & Md. Ibrahim H. Mondal, Synthesis of Highly Substituted Carboxymethyl Cellulose Depending on Cellulose Particle Size, 80 Int'l J Bio. Macromol. 725 (Year: 2015).*
Janagam, D.R. et al. "Nanoparticles for drug delivery to the anterior segment of the eye." Advanced Drug Delivery Reviews. Electronic publication on Apr. 6, 2017, vol. 122, pp. 31-64.

(Continued)

*Primary Examiner* — Sean M Basquill
(74) *Attorney, Agent, or Firm* — Insight Law Group, PLLC; Seung Lee

(57) ABSTRACT

The present disclosure provides a carrier composition for eye drops in which a substance to be delivered is loaded in a carrier, wherein the substance to be delivered includes one or more selected from the group consisting of an anti-inflammatory agent, a glaucoma treatment agent, a calcium channel blocker (CCB), an NMDA-receptor blocker, an antioxidant, a nitric oxide synthase inhibitor, a heat shock protein (HSP), a cystinosis treatment agent, and an antibiotic, the carrier has a spherical shape, the carrier includes a multilayer shell in a region ranging from the center to the surface of the carrier, the multilayer shell includes a core located in the center of the carrier and including a carboxymethyl cellulose (CMC)-based hydrogel having a degree of substitution (D.S.) of 0.9, a first shell located on the surface of the core and including a CMC-based hydrogel having a degree of substitution of 0.8, a second shell located on the surface of the first shell and including a CMC-based hydrogel having a degree of substitution of 0.6, and a third shell including a CMC-based hydrogel having a degree of substitution of 0.65, and the multilayer shell includes the core having a radius equal to 25% of the radial length of the carrier, the first shell having a thickness equal to 20% of the radial length, the second shell having a thickness equal to 40% of the radial length, and the third shell having a thickness equal to 15% of the radial length, and a pharmaceutical composition including the same.

8 Claims, 11 Drawing Sheets

(56) References Cited

OTHER PUBLICATIONS

Yamamoto, K. et al. "Core-multishell nanocarriers: Transport and release of dexamethasone probed by soft X-ray spectromicroscopy." Journal of Controlled Release. Electronic publication on Aug. 24, 2016. vol. 242, pp. 64-70.
International Search Report dated Apr. 14, 2020 for International Application No. PCT/KR2019/018642 and its English translation.
Written Opinion dated Apr. 14, 2020 for International Application No. PCT/KR2019/018642 and its English translation.

\* cited by examiner

CARRIER COMPOSITION FOR EYE DROPS AND PHARMACEUTICAL COMPOSITION INCLUDING THE SAME

CROSS-REFERENCE TO RELATED APPLICATIONS

This application is a National Phase Entry of International Application No. PCT/KR2019/018642, filed on Dec. 27, 2019, which claims priority and benefits of Korean Application Nos. 10-2018-0172598, filed on Dec. 28, 2018, and 10-2019-0176553, filed on Dec. 27, 2019, the content of which is incorporated herein by reference in their entirety.

TECHNICAL FIELD

The present disclosure relates to a carrier composition for eye drops and a pharmaceutical composition including the same, and more particularly, to a carrier composition for eye drops, which allows a substance to be delivered to stay in the anterior segment of an eye for a long time and slowly releases the substance to be delivered, thereby maintaining the medicinal effect of the substance to be delivered for a long period of time, and a pharmaceutical composition including the same.

BACKGROUND ART

The use of medicines such as anti-inflammatory drugs and antibiotics in small amounts and at low frequencies is one of the important concerns in the art because it helps in terms of drug abuse prevention, convenience and cost effectiveness.

Meanwhile, in the case of eye drop drugs, the rate of drug absorption after one administration is as very low as 5% or less of the amount administered, due to washing out of the drug by tears and the loss of the drug by eye blinking or the clarification of the drug by tears. Therefore, the eye drop drugs should be frequently administered.

In particular, it is necessary to administer anti-inflammatory eye drops to prevent infection and inflammation at the surgical site of the patient after cataract surgery or other ophthalmic surgery. In this case, for example, there is inconvenience in that an eye drop containing an anti-inflammatory drug or an antibiotic should be frequently applied dropwise to an eye 3 to 6 times a day for 1 month. In addition, if the timing of eye drop application is missed, side effects may occur. Therefore, there is a need to develop a technology that can effectively deliver eye drops to an eye and can maintain the efficacy of the eye drops for a long time.

The present inventors have developed a carrier composition, which is harmless and safe for the human body, allows a substance to be delivered to penetrate into tissue without pain, and enables the substance to be delivered to a local site at a high concentration, and a pharmaceutical composition including the same.

Korean Patent No. 10-0775065 relates to an eye drop composition having a long-lasting effect and a method for preparing the same, and merely discloses an eye drop composition which contains a carboxyvinyl polymer in an ophthalmic formulation, and thus exhibits prolonged drug duration time while giving a comfortable feeling when applied dropwise to an eye. However, it does not disclose a technology in which a hydrogel is composed of multilayer shell particles and is used as a drug carrier.

Korean Patent No. 10-0938500 relates to an eye drop composition for preventing and treating ophthalmic diseases, and merely discloses an eye drop composition containing hyaluronic acid and a salt thereof as active ingredients in addition to carboxymethyl cellulose. However, it does not disclose a technology in which a hydrogel, which stays locally in the anterior segment of an eye and sustainedly releases the drug for a long period of time, is composed of multilayer shell particles and is used as a drug carrier.

Meanwhile, a pharmaceutical composition should necessarily undergo a sterilization process. However, when a suspension gel contained in the pharmaceutical composition undergoes sterilization with a filter, changes in the contents of the excipient and the active ingredient are severe. For this reason, the suspension gel may not be subjected to sterilization with a filter.

Instead of sterilization with a filter, a high-temperature sterilization method is used to maintain the composition in a sterile state. However, in the case of a steroid-based drug or a derivative thereof, there is a fatal problem in that the denaturation of the drug at high temperature occurs. For this reason, technical development for this drug is impossible.

The present inventors have found a pharmaceutical composition which undergoes no change in the content of the active ingredient and no change in the component and content of the suspending agent phosphatidylcholine even after sterilization with a filter, thereby completing the present disclosure.

PRIOR ART DOCUMENTS

Patent Documents (Patent Document 0001) Korean Patent No. 10-0775065
(Patent Document 0002) Korean Patent No. 10-0938500

DISCLOSURE

Technical Problem

The present disclosure is intended to solve the above-described problems occurring in the prior art and other technical problems that have yet to be resolved.

An object of the present disclosure is to provide a carrier composition, which is capable of penetrating into a local eye site at a high concentration, and a pharmaceutical composition including the same.

Another object of the present disclosure is to provide a carrier composition for eye drops, which stays in the anterior segment of an eye for a long period of time and sustainedly releases an effective amount of a drug, and a pharmaceutical composition including the same.

Still another object of the present disclosure is to provide a carrier composition, which may prolong the duration of a drug and drastically reduce the number of eye drop applications, thereby increasing the patient's convenience, and a pharmaceutical composition including the same.

Yet another object of the present disclosure is to provide a composition, which enables easy sterilization of suspension eye drops, and a method for preparing the same.

Technical Solution

To achieve the above objects, the present disclosure provides a carrier composition for eye drops in which a substance to be delivered is loaded in a carrier, wherein the substance to be delivered includes one or more selected from the group consisting of an anti-inflammatory agent, a glaucoma treatment agent, a calcium channel blocker (CCB), an NMDA-receptor blocker, an antioxidant, a nitric oxide synthase inhibitor, a heat shock protein (HSP), a cystinosis treatment agent, and an antibiotic, the carrier has a spherical shape, the carrier includes a multilayer shell in a region ranging from the center to the surface of the carrier, the multilayer shell includes a core located in the center of the carrier and including a carboxymethyl cellulose (CMC)-based hydrogel having a degree of substitution (D.S.) of 0.9, a first shell located on the surface of the core and including a CMC-based hydrogel having a degree of substitution of 0.8, a second shell located on the surface of the first shell and including a CMC-based hydrogel having a degree of substitution of 0.6, and a third shell including a CMC-based hydrogel having a degree of substitution of 0.65, and the multilayer shell includes the core having a radius equal to 25% of the radial length of the carrier, the first shell having a thickness equal to 20% of the radial length, the second shell having a thickness equal to 40% of the radial length, and the third shell having a thickness equal to 15% of the radial length.

In the present disclosure, the anti-inflammatory agent may include one or more selected from the group consisting of dexamethasone, diclofenac, ketorolac, rimexolone and difluprednate.

In the present disclosure, the carrier composition may have an average particle diameter (D50) of 1 to 500 nm.

In the present disclosure, the carrier composition may inhibit inflammation or infection after surgery for ophthalmic disease.

In the present disclosure, the ophthalmic disease may be cataract.

In the present disclosure, the carrier composition undergoes no change in the contents of a hydrophobic drug and an excipient (suspending agent) even after sterilization through a 200 nm filter by imparting structural fluidity to the hydrophobic drug or a composite carrier of the hydrophobic drug.

The present disclosure also provides a pharmaceutical composition including the above-described carrier composition.

Advantageous Effects

The carrier composition according to the present disclosure has the effect of maintaining the efficacy of the substance to be delivered for a long time by slowly releasing the substance to be delivered for a long time.

The carrier composition according to the present disclosure has the effect of releasing a drug so that the drug stays in, particularly, the anterior segment of an eye. Thus, it is suitable for loading a drug that acts on the anterior segment.

In addition, since the carrier composition according to the present disclosure includes CMC-based hydrogel particles as a carrier, it does not cause eye damage or significant foreign body sensation even when applied dropwise to an eye, and thus gives comfortable feeling to the user.

The carrier composition according to the present disclosure enables the efficacy of the drug to be maintained for a long time even when it is applied dropwise to an eye once a day. Thus, the composition does not need to be frequently applied dropwise to an eye by the user, and thus may increase the user's convenience and the effect of treatment.

The carrier composition according to the present disclosure undergoes no change in the contents of a hydrophobic drug and an excipient (suspending agent) even after sterilization through a 200 nm filter by imparting structural fluidity to the hydrophobic drug or a composite carrier of the hydrophobic drug.

In addition, according to the present disclosure, a steroid-based drug having severe toxicity and side effects is used in drastically reduced amounts, so that the amount of the drug administered to the human body is reduced, thus reducing the toxicity of the drug.

MODE FOR DISCLOSURE

Figure 1:
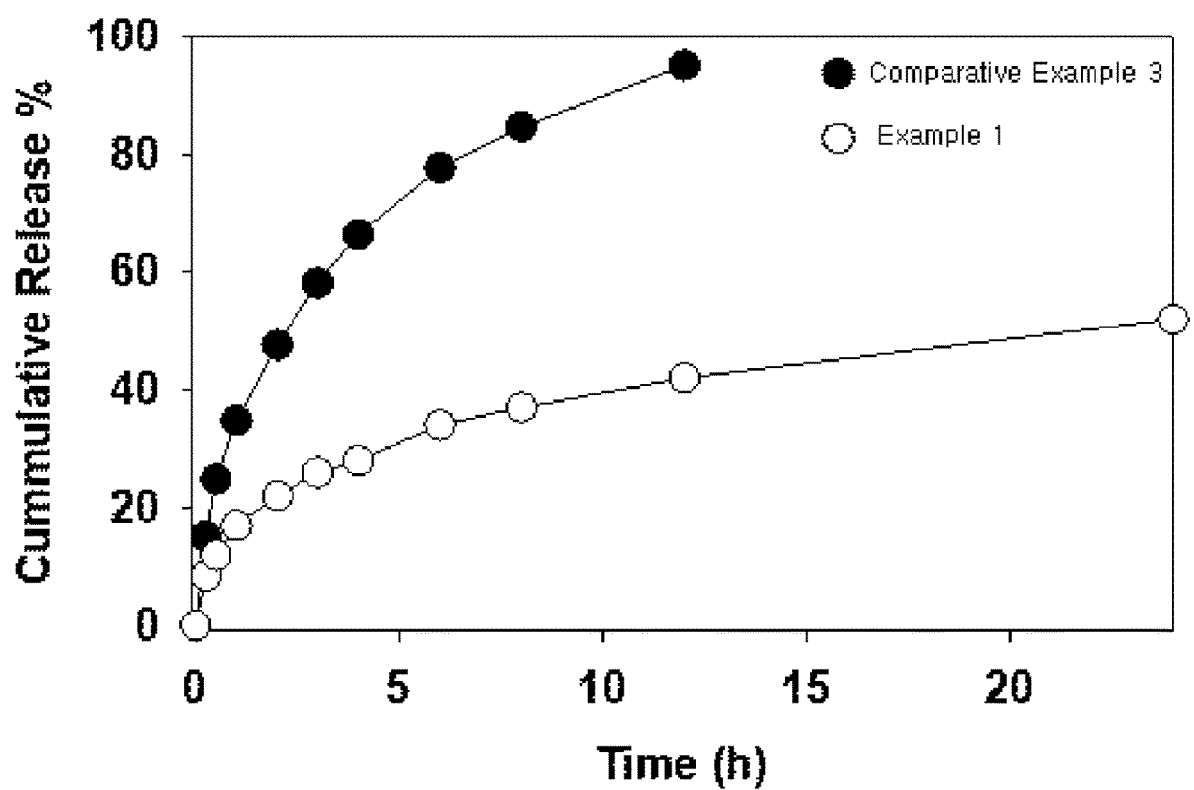
FIG. 1 shows results indicating the drug release effects of Example 1 and Comparative Example 3.

Hereinafter, each configuration will be described in more detail, but this is only one example, and the scope of the present disclosure is not limited by the following contents.

The present disclosure is directed to a carrier composition including a carrier, composed of hydrogels, and a substance to be delivered, in which the carrier composition gives comfortable feeling when applied dropwise to an eye, and at the same time, stays in the anterior segment of the eye for a long time and sustainedly releases the drug.

Specifically, the carrier composition for eye drops according to the present disclosure is a carrier composition for eye drops in which a substance to be delivered is loaded in a carrier, wherein the substance to be delivered includes one or more selected from the group consisting of an anti-inflammatory agent, a glaucoma treatment agent, a calcium channel blocker (CCB), an NMDA-receptor blocker, an antioxidant, a nitric oxide synthase inhibitor, a heat shock protein (HSP), a cystinosis treatment agent, and an antibiotic, the carrier has a spherical shape, the carrier includes a multilayer shell in a region ranging from the center to the surface of the carrier, the multilayer shell includes a core located in the center of the carrier and including a carboxymethyl cellulose (CMC)-based hydrogel having a degree of substitution (D.S.) of 0.9, a first shell located on the surface of the core and including a CMC-based hydrogel having a degree of substitution of 0.8, a second shell located on the surface of the first shell and including a CMC-based hydrogel having a degree of substitution of 0.6, and a third shell including a CMC-based hydrogel having a degree of substitution of 0.65, and the multilayer shell includes the core having a radius equal to 25% of the radial length of the carrier, the first shell having a thickness equal to 20% of the radial length, the second shell having a thickness equal to 40% of the radial length, and the third shell having a thickness equal to 15% of the radial length.

The carrier of the carrier composition according to the present disclosure may be composed of hydrogels. In particular, since CMC-based hydrogels having different degrees of substitution have different elasticities and strengths, they are characterized by having different drug loading amounts and release rates. Based on this characteristic, the present disclosure is characterized by using an artificial hydrogel carrier having a multilayer shell structure.

Carboxymethyl cellulose (CMC) is a material obtained from cellulose, a natural material, and is widely known to have an excellent moisturizing effect. It is also widely used as a material for insertion into the human body, is harmless even when contained in eye drops, and is used as a replacement material for the human body in various medical fields.

In the present disclosure, the CMC, which has been previously recognized to be useful as eye drops and safe, is used intact, and fine hydrogel particles are produced using the CMC and used as eye drops. Thus, the present disclosure provides a carrier composition having guaranteed safety for the human body.

In particular, the carrier according to the present disclosure includes a multilayer hydrogel obtained using CMC-based hydrogels having different degrees of substitution.

The degree of substitution of the CMC is a value that affects the viscosity and physical properties of the CMC, and refers to the average number of carboxymethyl groups substituted per anhydroglucose unit.

Specifically, the carrier has a spherical shape so as to cause no damage to an eye even after applied dropwise to the eye. The carrier has a structure including a multilayer shell in a region ranging from the center to the surface of the carrier.

The multilayer shell includes a core located in the center of the carrier and including a CMC-based hydrogel having a degree of substitution of 0.9, a first shell located on the surface of the core and including a CMC-based hydrogel having a degree of substitution of 0.8, a second shell located on the surface of the first shell and including a CMC-based hydrogel having a degree of substitution of 0.6, and a third shell including a CMC-based hydrogel having a degree of substitution of 0.65.

The CMC-based hydrogel is a gel formulation obtained by dissolving powdery CMC in water to increase the viscosity, and is generally prepared in a patch or sheet form, which is used as a mask pack or a patch. For use in the present disclosure, the CMC-based hydrogel is formed into spherical particles which are then coated with shells to form multilayer shell structures.

The viscosity of the CMC varies depending on the degree of substitution of the molecule thereof and the concentration of a solution containing the same. In the present disclosure, there are used hydrogels prepared to have different degrees of substitution while maintaining the concentration of the CMC in an aqueous solution at 10%.

Specifically, the third shell constituting the outermost layer is a first portion coming into contact with the outside, and should allow the initial drug release to be maintained at a predetermined level, and, at the same time, should be prevented from being easily degraded. Since the second shell having lower elasticity is located inside the third shell, the maintenance time of the third shell greatly influences the initial release and sustained release of the substance to be delivered. This is because the second shell loads the largest amount of the substance to be delivered, and thus may come into contact with an eye or tears and easily release the substance to be delivered.

Therefore, the third shell includes a hydrogel obtained from a CMC having a degree of substitution of 0.65, and the second shell includes a hydrogel obtained from a CMC having a degree of substitution of 0.6.

As the third shell having higher elasticity and hardness is located at the outermost layer, even if the hardness of the inner shell is weakened by absorbing water, the third shell is relatively firmly held, thereby delaying the time that the second shell is directly exposed to the outside.

After eye drop application, the hydrogel matrix of the third shell is softened by the body temperature and releases the substance to be delivered. When external tears or the solvent of the pharmaceutical composition penetrates into the second shell through the softened matrix, the second shell is also softened and releases the substance to be delivered through the third shell. Thus, the substance to be delivered is released mainly from the third shell at an initial stage and released from the third shell and the second shell with the passage of time.

At about 4 to 5 hours after eye drop application, the third shell constituting the outermost layer is swollen, separated from the carrier, and degraded into small pieces. As the second shell also releases the substance to be delivered during the maintenance of the third shell, the release of the substance to be delivered becomes 60 to 70% or more in a state in which the third shell has been degraded and the second shell is located at the outermost surface. When the second shell becomes a state in which it is located at the outermost surface, external water penetrates into the first shell, the first shell is swollen, and the substance to be delivered starts to be released slowly from the swollen first shell.

As the second shell is composed of a hydrogel having low hardness, it is swollen and degraded within about 3 hours, and a portion of the first shell starts to be exposed to the outside.

In a state in which the first shell having a higher elasticity and hardness than the third shell is exposed to the outermost surface, the first shell slowly releases the substance to be delivered, and releases the substance to be delivered for the longest times while the shape of the shell is maintained. The first shell is also degraded slowly while releasing the substance to be delivered over about 8 to 9 hours.

The first shell may be formed by adding the substance to be delivered to a hydrogel during hydrogel preparation, followed by gelling. Specifically, the first shell may be formed by adding 20 parts by weight of the substance to be delivered to 100 parts by weight of a CMC-based hydrogel having a degree of substitution of 0.8, followed by gelling.

If the substance to be delivered is added in larger amounts than the above-described amount, a problem arises in that the amount of the substance to be delivered, which is loaded in the first shell, is limited compared to the amount of substance added, and thus the substance to be delivered is consumed except for the loaded amount of the substance to be delivered, thus reducing the efficiency with which the carrier composition is produced. If the substance to be delivered is added in smaller amounts than the above-described amount, a problem arises in that the release time of the substance to be delivered is shortened to about 3 hours, and thus the effect of releasing the substance to be delivered is not maintained for a long time.

While a portion of the first shell starts to be exposed to the outside, the first shell starts to be swollen and external tear or the solvent penetrates into the core through the first shell. The core is swollen and maintained inside the first shell, and the substance to be delivered loaded in the core is held without being released through the first shell.

At about 20 hours after eye drop application, a portion of the first shell is degraded and a portion of the core starts to be exposed. At this time, the substance to be delivered starts to be released. The substance to be delivered loaded in the core is released for about 4 to 5 hours, and as the size of the core gradually decreases and the surface area thereof decreases, the effect of releasing the substance to be delivered becomes little after about 6 hours.

Like the first shell, the core is also loaded with the substance to be delivered by adding the substance to be delivered to a hydrogel during hydrogel preparation and forming a gel.

The core may be formed by adding 40 parts by weight of the substance to be delivered to 100 parts by weight of the hydrogel to be included in the core, and gelling the mixture.

The reason why the substance to be delivered is added in a larger amount than the amount of substance to be delivered added to the first shell is because the hardness of the core is higher and the hydrogel matrix is densely formed, and thus the release of the substance to be delivered may be relatively easily achieved.

Even though the core has a dense hydrogel matrix, the release rate of the substance to be delivered from the core may be the same as the release rate from the first shell. Therefore, if the substance to be delivered is added in smaller amounts than the above-described amount, a problem arises in that the release of the substance to be delivered is small, and thus the substance to be delivered cannot exhibit an effective pharmacological effect, and if the substance to be delivered is added in larger amounts than the above-described amount, a problem arises in that the hardness of the core is reduced, making it not easy to introduce the first shell to the surface of the core.

Meanwhile, the multilayer shell may include the core having a radius equal to 25% of the radial length of the carrier, the first shell having a thickness equal to 20% of the radial length, the second shell having a thickness equal to 40% of the radial length, and the third shell having a thickness equal to 15% of the radial length.

This structure has a great influence on the release rate of the substance to be delivered.

The configuration as described above is such that the substance to be delivered loaded in the carrier is released at a substantially constant level over a long time after application to an eye. As the components of the carrier are configured to have the above-described thicknesses, the release rate of the substance to be delivered is maintained at a constant level.

Specifically, since the third shell is located at the outermost surface and has the largest contact area with the outside, it is preferably configured to have the above-described thickness. If the third shell has a smaller thickness than the above-described thickness, a problem will arise in that the third shell is swollen rapidly in an initial stage and the initial release of the substance to be delivered greatly increases, and thus the effect of releasing the substance to be delivered for a long time is reduced. If the third shell has a larger thickness than the above-described thickness, a problem will arise in that excessive time is required until the second shell is swollen through the third shell and the substance to be delivered is released.

In particular, this problem leads to a problem in that the release of the substance to be delivered decreases rapidly and the effect of the substance to be delivered greatly decreases.

The second shell is a shell having the largest thickness and is composed of the softest formulation. Accordingly, the second shell is degraded simultaneously with the release of the substance to be delivered, and thus the thickness of the second shell decreases with the passage of time. If the second shell has a larger thickness than the above-described thickness, a problem will arise in that the sizes of the first shell and the core relatively decrease, and the late-stage release of the substance to be delivered decreases rapidly.

The first shell constitutes the hardest shell except for the core, and serves to release the substance to be delivered for a long time in addition to the second shell. If the first shell has a larger thickness than the above-described thickness, a problem will arise in that the core is swollen and releases the substance to be delivered through the first shell and the release rate of the substance to be delivered increases, and thus the release time of the substance to be delivered becomes relatively short. As a portion of the first shell is removed and the core is exposed to the outside, the substance to be delivered is released early, and thus the release per hour increases and the release time becomes shorter.

According to one embodiment of the present disclosure, the carrier composition may have an average particle diameter (D50) of 1 to 500 nm. When the carrier composition has an average particle diameter within this range, it may easily pass through cells.

Meanwhile, the substance to be delivered is a substance which is delivered to an eye through eye drops and directly exhibits a pharmacological effect. Specifically, the substance to be delivered may include at least one selected from the group consisting of an anti-inflammatory agent, a glaucoma treatment agent, a calcium channel blocker (CCB), an NMDA-receptor blocker, an antioxidant, a nitric oxide synthase inhibitor, a heat shock protein (HSP), a cystinosis treatment agent, and an antibiotic.

For example, the anti-inflammatory agent may include at least one selected from the group consisting of dexamethasone, diclofenac, ketorolac, rimexolone and difluprednate. The glaucoma treatment agent may include at least one selected from the group consisting of pilocarpine, carbachol, epinephrine and dipivefrine, and the antibiotic may include tobramycin. In terms of the effect of the present disclosure, the anti-inflammatory agent is preferably dexamethasone.

The carrier composition according to one embodiment of the present disclosure may be used to inhibit inflammation or infection after surgery for ophthalmic disease, and the ophthalmic disease may preferably be cataract.

There is risk of inflammation and infection at the surgical site after surgery of cataract, and hence treatment with eye drops containing an anti-inflammatory agent, an antibiotic or the like is essential for the prevention of the inflammation or infection. However, frequent eye drop application (about 3 to 5 times a day) is generally required, and hence the user is inconvenient due to frequent eye drop application. If the timing of eye drop application is missed, the drug treatment efficiency may be lowered, and thus the risk of occurrence of side effects by infection or inflammation after cataract surgery may increase.

The present disclosure is intended to solve the above-described problems, and provides a carrier composition capable of exhibiting a medicinal effect of effectively preventing inflammation or infection after glaucoma surgery while improving the user's convenience.

When the carrier composition according to the present disclosure is used, it acts non-invasively, so there is little risk of infection, and the user can easily use the carrier composition.

The carrier composition according to the present disclosure may be configured such that the surface is electrically charged, if necessary. When the carrier composition is configured to have a positive or negative charge rather than a neutral state, the retention time of the carrier composition in the anterior segment of an eye may further increase, and the carrier composition may easily penetrate into the eye drop layer. As the carrier composition penetrates into the eye drop layer, the effect of delivering the substance to be delivered to an eye further increases.

The carrier composition of the present disclosure is effective in that the residence time thereof in the anterior segment of an eye is longer than that of a conventional pharmaceutical composition. In a state in which the surface composed of a human body-friendly hydrogel is somewhat swollen by absorbing water, the carrier composition foams a fine network on the eye surface by mutual attraction, thereby preventing the carrier composition from easily moving to the posterior segment.

The present disclosure also provides a pharmaceutical composition including the above-described carrier composition, an additive and an aqueous vehicle. Specifically, the additive may be one or more selected from the group consisting of a solubilizing agent and a thickener. The solubilizing agent may be phosphatidylcholine, and the thickener may be carboxymethyl cellulose (CMC) or glycerol.

In addition, the additive may be used without limitation, as long as it is an additive, such as a suspending agent, an isotonic agent, an adsorption preventing agent, a sulfur-containing reducing agent, a cryoprotective agent, or the like, which is generally used in the art.

The aqueous vehicle refers to an aqueous medium which is used to carry the carrier composition, and may be any aqueous medium which is not harmless to the human body. In this case, the formulation may be in the form of a solution in an oily or aqueous medium, a suspension, a syrup or an emulsion, and may further include a dispersing agent or a stabilizer.

The aqueous vehicle may preferably be saline or distilled water. The reason is to use an aqueous solvent in consideration of the physical properties of the carrier composition.

Eye tissue includes not only corneal, sclera, iris, ciliary body, choroid, inner coat, lens, vitreous body, and retina, but also the surrounding tissue of the eye. Examples of the surrounding tissue of the eye include, but are not limited to, conjunctivas such as upper eyelid conjunctiva, ocular conjunctiva, lower eyelid conjunctiva, superior conjunctiva, eyeball conjunctiva, upper eye periphery skin conjunctiva, lower eye periphery skin conjunctiva, eyeball conjunctiva, and inferior conjunctiva, sclera, sub-Tenon's space, and the like.

The eye tissue may be anterior segment tissue, specifically conjunctiva, sub-conjunctiva, superior fornix, inferior fornix, subconjunctival limbus, or the like, but is not limited thereto.

Penetration into eye tissue includes not only penetration into eye tissue, but also spreading to the surrounding tissue of the eye. For example, "penetration into eye tissue" may be penetration on or within the sclera (episcleral), beneath or within overlying tissues such as the subconjunctival tissue, e.g. at or near the limbus, within the periocular region, within the conjunctival cul-de-sac, within the sub-Tenon's space either anterior and/or posterior, but is not limited thereto.

The release of the substance to be delivered from the carrier composition may occur after the carrier composition penetrates into eye tissue.

The release rate of the substance to be delivered may be adjusted by the mixing ratio between the carrier and the substance to be delivered contained in the carrier composition. The release rate may increase as the proportion of the substance to be delivered contained in the carrier composition increases, and may decrease as the proportion of the substance to be delivered decreases.

According to one embodiment of the present disclosure, the mixing ratio between the carrier and the substance to be delivered contained in the carrier composition may be 1:0.1 to 1:5 by weight. For example, the mixing ratio between the carrier and the substance to be delivered may be 1:1 or 1:2.

In this case, the substance to be delivered may be loaded in the first shell layer by adding the substance during synthesis of a hydrogel in the step of preparing the core and the first shell, and may be loaded in the second shell and the third shell by preparing the respective hydrogel layers and then immersing the hydrogel layers in the respective solutions containing the substance to be delivered for 5 to 6 hours.

However, in consideration of the water absorption property of the hydrogels, the substance to be delivered is loaded through a process of immersing the hydrogel layers for 30 minutes and then drying the hydrogel layers for 5 minutes so as to prevent each shell from being degraded.

Hereinafter, the present disclosure will be described in detail with reference to examples. These examples are merely examples of the present disclosure, and the scope of the present disclosure is not limited thereto.

Preparation Example 1—Preparation of Carrier Composition

CMCs were added to and dissolved in water at a concentration of 10 wt %. Then, when gel formulations were formed, they were freeze-dried to form a spherical carrier having a multilayer shell structure. Specifically, a CMC having a degree of substitution of 0.9 for preparation of a core, a CMC having a degree of substitution of 0.8 for preparation of a first shell, a CMC having a degree of substitution of 0.6 for preparation of a second shell, and a CMC having a degree of substitution of 0.65 for preparation of a third shell, were used to prepare the respective hydrogels.

The core was prepared by adding 40 parts by weight of dexamethasone sodium phosphate to 100 parts by weight of a hydrogel in a stirring step for homogenization of the hydrogel, and the first shell was also prepared by adding 20 parts by weight of dexamethasone sodium phosphate to 100 parts by weight of a hydrogel in the same step.

After a hydrogel carrier precursor was prepared by sequentially stacking the first shell, the second shell and the third shell on the surface of the core, it was freeze-dried, thereby preparing a final carrier. The obtained carrier had a diameter of about 190 nm (a radial length of 100 nm). The carrier was sectioned vertically and the particle size thereof was examined by SEM images, interfaces resulting from the difference in molecular weight and the difference in texture were confirmed, and it was confirmed that a carrier having a multilayer shell structure was prepared in which a core having a diameter of about 50 nm, a first shell having a thickness of 20 nm, a second shell having a thickness of about 40 nm and a third shell having a thickness of about 15 nm were sequentially stacked.

Using the CMCs shown in Table 1 below, carriers having a multilayer shell structure according to Examples and Comparative Examples were prepared in the same manner as Preparation Example 1.

TABLE 1

| Degree of substitution of CMC | Example 1 | Example 2 | Comparative Example 1 | Comparative Example 2 | Comparative Example 3 | Comparative Example 4 |
|---|---|---|---|---|---|---|
| Core | 0.9 | 0.92 | 0.9 | 0.6 | 0.9 | 0.65 |
| First shell | 0.8 | 0.8 | 0.6 | 0.8 | 0.8 | 0.8 |
| Second shell | 0.6 | 0.6 | 0.8 | 0.9 | 0.65 | 0.6 |
| Third shell | 0.65 | 0.65 | 0.65 | 0.65 | 0.6 | 0.9 |
| Remarks | — | — | — | — | — | Carrier was collapsed after freeze drying |

Unlike other Examples and Comparative Examples, in Comparative Example 2, core particles were not produced, and hence a spherical multilayer shell structure was not foamed.

Preparation Example 2—Carrier Composition and Pharmaceutical Composition

With reference to Preparation Example 1 and Table 1 above, a hydrogel precursor intermediate including a core, a first shell and second shell was prepared. Next, the hydrogel precursor intermediate was immersed in a solution containing dexamethasone sodium phosphate dissolved therein (a solution having a concentration of 20%) for about 30 minutes, and then freeze-dried. Then, a third shell was stacked on the freeze-dried hydrogel precursor which was then immersed again in a solution containing dexamethasone sodium phosphate dissolved therein (a solution having a concentration of 20%), thereby preparing a carrier composition.

With reference to Table 2 below, anti-inflammatory eye drop compositions including the carrier compositions of the Examples and the Comparative Examples, respectively, were prepared.

TABLE 2

| | | Per g of pharmaceutical composition | |
|---|---|---|---|
| Active ingredient | Component names Carrier composition | Amount (mg) Dexamethasone sodium phosphate content: about 1.00 mg (loading amount) | Remarks |
| Thickener | Carboxymethyl cellulose | 3.00 | |
| Base material | Zinc sulfate heptahydrate | 0.200 | 200 ppm concentration |
| Base material | Phosphatidylcholine | 0.600 | 600 ppm concentration |
| Thickener | Glycerin | 25.00 | Medical grade |
| Preservative | Chlorobutanol | 2.50 | GMP (permissible range: 0.25 to 0.5%) |
| pH adjusting agent | Hydrochloric acid | q.s. | |
| pH adjusting agent | Sodium hydroxide | q.s. | |
| Solvent | Purified water | q.s. 1,000 (1.0 g) | |

Preparation Example 3—Carrier Composition and Pharmaceutical Composition

With reference to Table 3 below, an anti-inflammatory eye drop composition of Example 3, which includes the carrier composition of Example 1, was prepared in the same manner as Preparation Example 2.

TABLE 3

| | | Per g of pharmaceutical composition | |
|---|---|---|---|
| Active ingredient | Component names Carrier composition | Amount (mg) Dexamethasone sodium phosphate content: about 1.00 mg (loading amount) | Remarks |
| Thickener | Carboxymethyl cellulose | 3.00 | |
| Base material | Zinc sulfate heptahydrate | — | |
| Base material | Phosphatidylcholine | 0.600 | 600 ppm concentration |
| Thickener | Glycerin | 25.00 | Medical grade |
| Preservative | Chlorobutanol | 2.50 | GMP (permissible range: 0.25 to 0.5%) |
| pH adjusting agent | Hydrochloric acid | q.s. | |
| pH adjusting agent | Sodium hydroxide | q.s. | |
| Solvent | Purified water | q.s. 1,000 (1.0 g) | |

Test Example 1—Drug Release Test

[Test Method]
Analysis instrument

TABLE 4

| | |
|---|---|
| Instrument | Agilent 1260 HPLC systems with RI and DAD detector |
| Column | L1, 4 mm × 300 mm or a column similar thereto |
| Eluent | Methanol (0.01M potassium dihydrogen phosphate solution):water = 1:1 |
| Analysis time | 30 min |
| Calibration | Agilent easyvial systems |
| Standard materials | Dexamethasone sodium phosphate (USP grade) |
| Injection volume | 20 μL |
| Detector | 254 nm (measurement wavelength) |
| Flow rate | 1.6 ml/min |

Test standard: in accordance with USP method "Dexamethasone Sodium Phosphate Ophthalmic Solution".

Standard solution preparation: a mobile phase solution was added to 9 mg of dexamethasone sodium phosphate to make a volume of 100 ml.

Preparation of test solution: a mobile phase was added to 4 mg of dexamethasone phosphate to make a volume of 50 ml.

[Operation and Calculation]
System Suitability Determination

When the standard solution prepared by the above-described method is repeatedly measured 6 times, the relative standard deviation (RSD) of the main peaks is 1.5% or less.

% of dexamethasone phosphate=$[(A_T \times C_S) \times 472.44]/[(A_S \times C_T) \times 516.40]$    [Calculation equation]

$A_T$: the peak area of the main peak in the test solution
$C_S$: the amount (mg) of standard product collected
$A_S$: the average peak area of the main peaks in the standard solution
$C_T$: the amount (mg) of test sample collected
P: the purity of the standard product
472.44: the molecular weight of dexamethasone phosphate
516.40: the molecular weight of dexamethasone sodium phosphate

[Release Test]

1 ml of eye drops prepared according to a preparation process was filled in Float-A-lyzer® (spectra/Por®, RC membrane, MWCO=1,000) which was then immersed in the drug release medium saline solution (100 ml). Then, a drug release test was performed for predetermined times of 0, 0.5, 1, 2, 3, 4, 6, 8, 12 and 24 hours.

100 ml of the drug release medium was completely freeze-dried to obtain solid powder, and the drug was extracted by adding ethanol to the powder and analyzed. The results are shown in FIG. 1.

[Test Results]

FIG. 1 shows the results of the drug release test for Example 1 (○) and Comparative Example 3 (●). The test results were obtained for the carrier composition having a fast drug release rate in vitro due to the property of the eye drop drug which is rapidly washed out by tears, and for the carrier composition that can slowly release the drug for 24 hours.

In particular, in the case of Comparative Example 3, the release of the drug increased rapidly while the surface of the carrier was degraded fast.

Test Example 2—Test for Analysis of Particle Size Distribution and Particle Size Change after Filter Test

[Test Method]
Particle size measurement instrument: Malvern Nano ZS model

Content measurement instrument: the same as that in Test Example 1

Measurement condition: a sterilized sample was treated at a concentration of 0.1% (on a drug basis), and the particle size thereof was measured.

Zeta potential: zeta potential was measured using a disposable cell (Malvern) for zeta potential measurement.

[Measurement Results]

Figure 2:
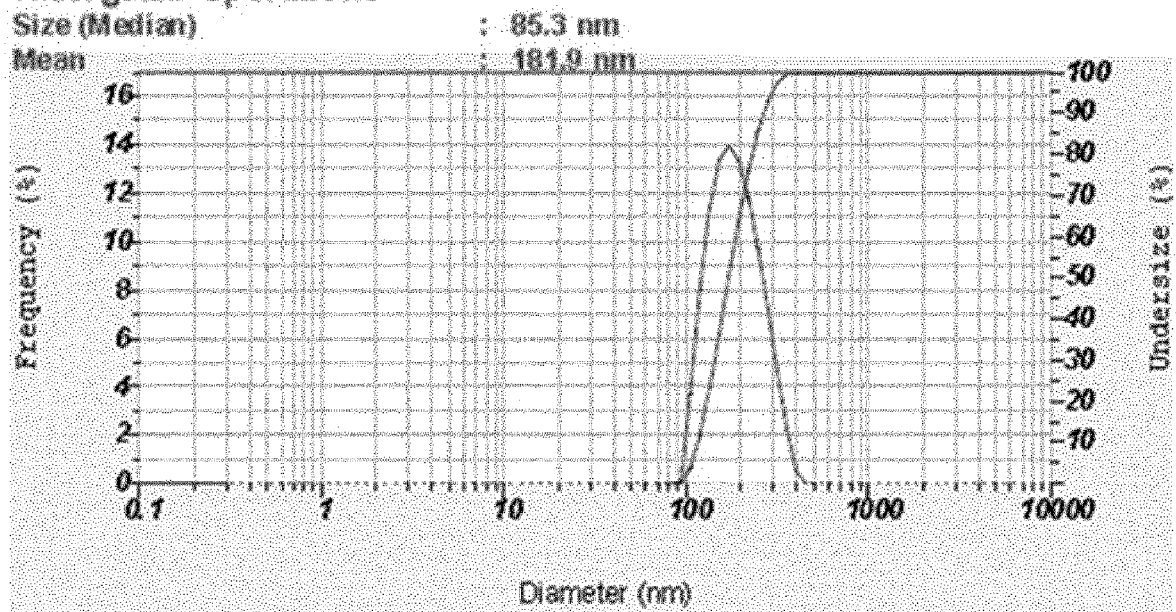
FIGS. 2 and 3 show results indicating the particle size distributions of carriers of Examples 1 and 2 before a filter test.
Figure 3:
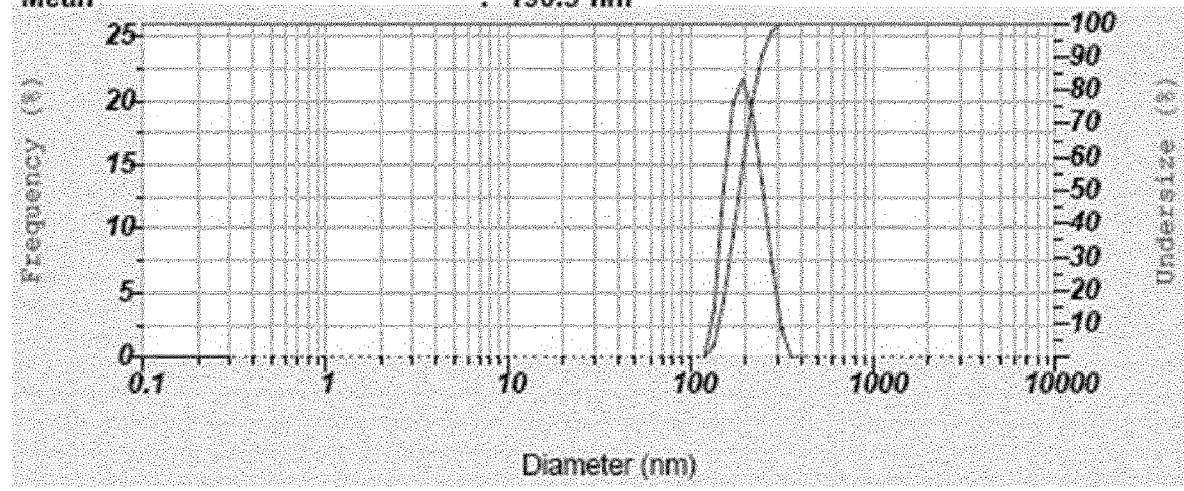

The particle size distributions of Examples 1 and 2 were measured by the Korea Testing & Research Institute (KTR), and the results are shown in FIGS. 2 and 3. It was confirmed that the average particle size was maintained at about 190 nm even after sterilization with a filter.

Figure 4:
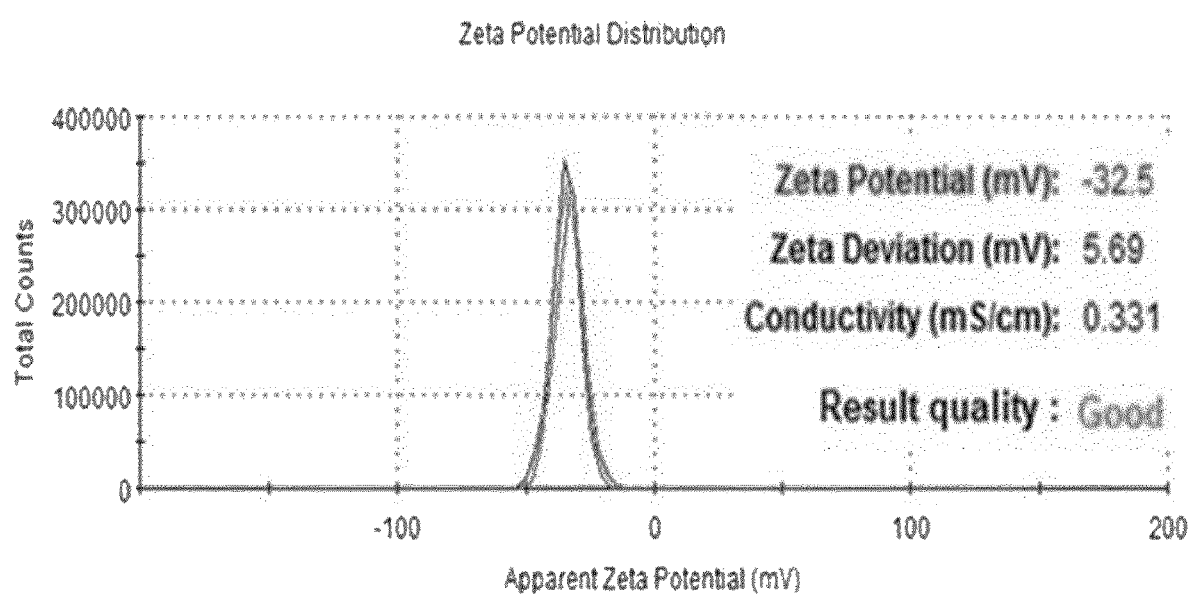
FIG. 4 shows the results of measuring zeta potential for a carrier of Example 1.

The zeta potential was measured to be −32.5 mV, and the results of measuring the zeta potential are shown in FIG. 4. It was confirmed that the particles were nanoparticles having a strong anionic charge. Therefore, it can be seen that the nanoparticles were uniformly dispersed without entanglement in the suspension formulation and exhibited a very stable potential value.

Figure 5:
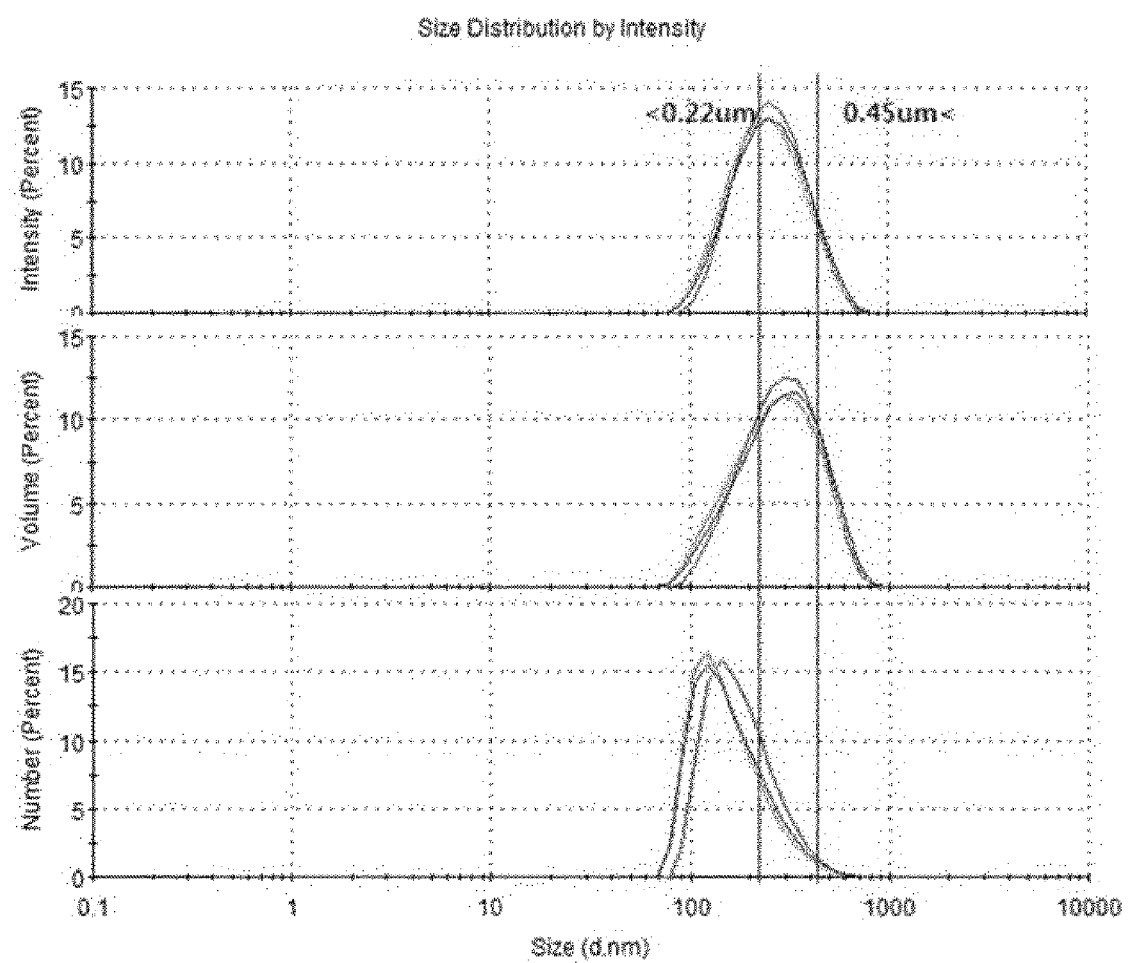
FIG. 5 shows results indicating the particle size distribution of a carrier of Example 2 after a filter test.

The carrier composition of Example 2 was sterilized with a filter, and then the particle size distribution thereof was analyzed in-house using the Malvern instrument. The results of the analysis are shown in FIG. 5. It was confirmed that the carrier composition showed a uniform particle size distribution even after the sterilization with a filter.

TABLE 5

| | |
|---|---|
| Instrument | Agilent 1260 HPLC systems with RI and DAD detector |
| Column | L1, 4 mm × 300 mm or a column similar thereto |
| Eluent | Methanol (0.01M potassium dihydrogen phosphate solution):water = 1:1 |
| Analysis time | 30 min |
| Calibration | Agilent easyvial systems |
| Standard materials | Dexamethasone sodium phosphate (USP grade) |
| Injection volume | 20 μl |
| Detector | 254 nm (measurement wavelength) |
| Flow rate | 1.6 ml/min |

Test standard: in accordance with USP method "Dexamethasone Sodium Phosphate Ophthalmic Solution".

Standard solution preparation: a mobile phase solution was added to 9 mg of dexamethasone sodium phosphate to make a volume of 100 ml.

Preparation of test solution: a mobile phase was added to 4 mg of dexamethasone phosphate to make a volume of 50 ml.

[Operation and Calculation]
System Suitability Determination

When the standard solution prepared by the above-described method is repeatedly measured 6 times, the relative standard deviation (RSD) of the main peaks is 1.5% or less.

The change in the drug content between before and after the filter test was measured in the same manner as Test Example 2, and the change values relative to the content before the test are shown in Table 6 below.

Test substances: pharmaceutical compositions of Examples and Comparative Examples Test method: quantitative analysis was performed using a LabAssay phospholipid test kit (Fujifilm Wako Pure Chemical Corporation). (Code number=997-01801).

Test instrument: Microplate reader (Biotek, Epoch-2)

Test method: the test substances were analyzed using the test method (Phospholipids C, Choline oxidase-DAOS method) and procedure provided by Wako.

TABLE 6

| | Example 1 | Example 2 | Example 3 | Comparative Example 1 | Comparative Example 2 | Comparative Example 3 | Comparative Example 4 |
|---|---|---|---|---|---|---|---|
| Change (%) in content of active ingredient | −0.5 ± 0.1 | −0.4 ± 0.2 | −0.3 ± 0.08 | −6 ± 4.0 | | −22 ± 5.6 | −15 ± 7.8 |
| Change (%) in content of suspending agent | −1.14 ± 0.2 | −1.01 ± 0.5 | −0.57 ± 0.1 | −13.0 ± 2.9 | — | −24.0 ± 3.8 | −18 ± 6.1 |

Referring to Table 6 above, in the case of the Examples, only the change within the error range was confirmed, but in the case of the pharmaceutical compositions including the carrier compositions of Comparative Examples 1, 3 and 4, respectively, it can be seen that the content of the drug after the filter test decreased greatly.

In addition, in the case of the Examples, only the change in the content of the suspending agent within the error range was confirmed, suggesting that there was little or no change in the content of the suspending agent, whereas in the case of the Comparative Examples, it can be seen that the content of the suspending agent decreased greatly.

Test Example 4—Drug Release Test and Pharmacokinetic Test Using Rabbits

A test for confirming the drug release effect of the anti-inflammatory eye drop composition prepared according to Preparation Example 2 was conducted.

[Test Method]

TABLE 7

| | |
|---|---|
| Species and lineage | New Zealand white rabbits (clean animals) |
| Number and body weight (when purchased) of animals | 17 animals (male), 1.941 to 2.459 kg |
| Number and body weight (when administered) of animals | 14 animals (male), 2.199 to 2.687 kg |

1. Quarantine and Acclimation

NZW rabbits were selected because these rabbits are an animal species that make it possible to predict outcomes in humans due to their similarity of eye size and structure to those of humans and many comparable studies thereon are accumulated.

When the animals were carried in, visual inspection of the animals was performed and the body weights thereof were measured. General symptoms of the animal were observed once daily during the acclimation period. All the animals were allowed to acclimate for 5 days to acclimate to the laboratory environment.

2. Individual Identification

For individual identification, the animal number was written on the inside of the left ear canal using a red marker pen during the acclimation period. To each breeding cage, a cage identification card containing the test number, test substance, test item, date of acquisition, test period, sex/animal number and the person in charge of the test was attached.

3. Individual Selection

The body weights were measured on the day of start of administration, and then among the animals having a body weight of 2.0 to 3.0 kg, healthy animals with clean eyes were selected after eye inspection.

4. Treatment of Remaining Animals

Remaining animals were excluded from the test system after grouping, anesthetized by administering Zoletil50® intravenously after the day of start of the confirmation test, and then euthanized by cardiac arrest induced by KCl administration.

5. Ethics Committee

All experimental procedures were approved by the Animal Care and Use Review Committee of Hoseo University (HUACUC) (approval number: HUACUC-18-66).

6. Breeding Conditions

Breeding conditions were the same for all the animals, and the animals were housed in an animal room maintained at a temperature of 18.5 to 24.0° C., a relative humidity of 35.8 to 69.8%, 10 to 15 ventilations/hour, a 12-hr light/12-hr dark cycle/day (7 am to 7 pm), and an illumination density of 150 to 300 lux. Each animal was housed and bred in a breeding cage having a size of 570×650×335 mm.

Solid feed (Altromin 2013) was put into a feeder, and Asan-si tap water was placed in a drinking water bottle after sterilized by UV light. The animals were allowed to freely access the feed and the water.

7. Eye Drop Application

The amount of test substance was 1 drop when a vial containing the test substance was used. The test substance was applied dropwise to both eyes of each test animal in equal amounts. The lower eyelid was pulled to make a cup shape, and then the test substance was applied dropwise to the eye. After the eye drop application, the upper and lower eyelids were held together for 3 to 5 seconds such that the test substance would not be lost.

8. Test Method

At 0.5, 1, 2, 6, 12, 18 and 24 hours after the test substance was applied dropwise to the eye, the aqueous humor was collected. The test animals were anesthetized by administering a 3:1 mixture of ketamine (Yuhan ketamine 50®) and xylazine (Rompun, Bayer) into the ear vein. At 5 minutes after the anesthesia, the aqueous humor was collected using a 30 G syringe needle. About 150 μL of the aqueous humor was collected from each eye.

[Analysis of Results]

1. Pretreatment of test sample

100 μl of the collected aqueous humor and 100 μl of acetonitrile were mixed with each other, and then vortexed using a vortex mixer for 1 minute. Then, the mixture was centrifuged at 3,000 rpm and 4° C. for 20 minutes, and 100 μl of the supernatant was collected and used in analysis.

2. Analysis Instrument and Conditions

TABLE 8

| Instrument used | LC (Waters UPLC) |
| --- | --- |
| | MS/MS (Thermo Scientific TSQ Quantum Ultra) |
| Column | Phenomenex Kinetex 2.6 μm, C18 100A, |
| | 100 × 2.1 mm |
| Mobile phase | 0.1% MeOH: 5 mM ammonium acetate = 20:80 |
| Flow rate | 0.2 mL/min |
| m/s | 472.8 →435.14 |
| Tube lens | 78 |
| Collision E | 18 |
| Ion mode | Positive ion |
| Spray voltage | 4,500 |

[Analysis Results]

TABLE 9

| Standard | Area | RT (minutes) |
| --- | --- | --- |
| 10 | 1,573 | 1.45 |
| 50 | 24,746 | 1.63 |
| 100 | 61,612 | 1.55 |
| 200 | 136,868 | 1.53 |
| 500 | 385,737 | 1.53 |

Figure 6:
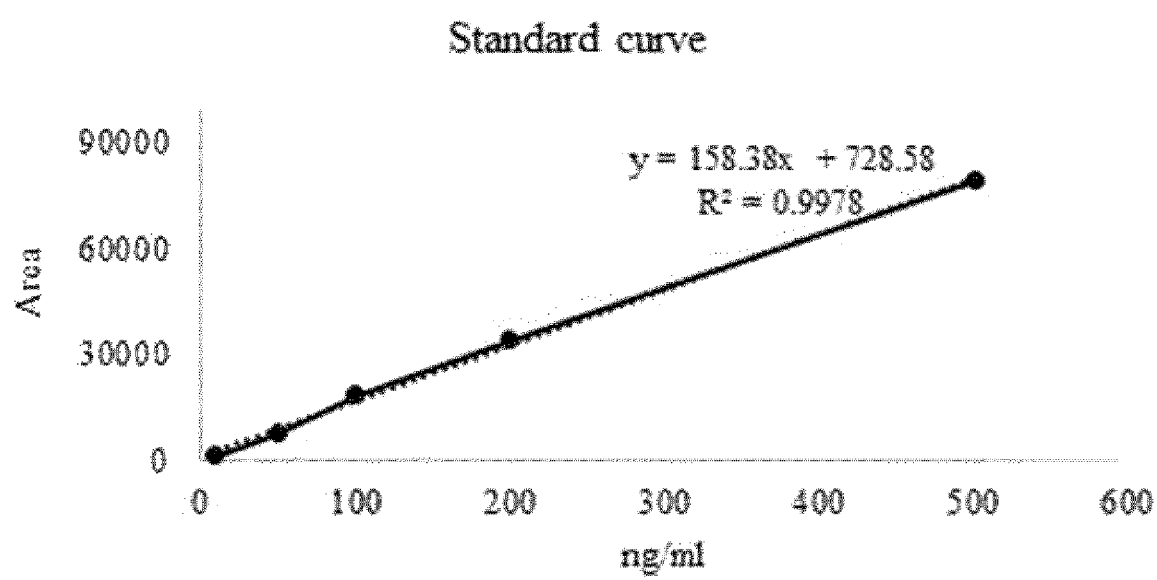
FIG. 6 is a graph showing the results of calibration performed using the result values shown in Table 7 to calculate the amount of drug released.
Figure 7:
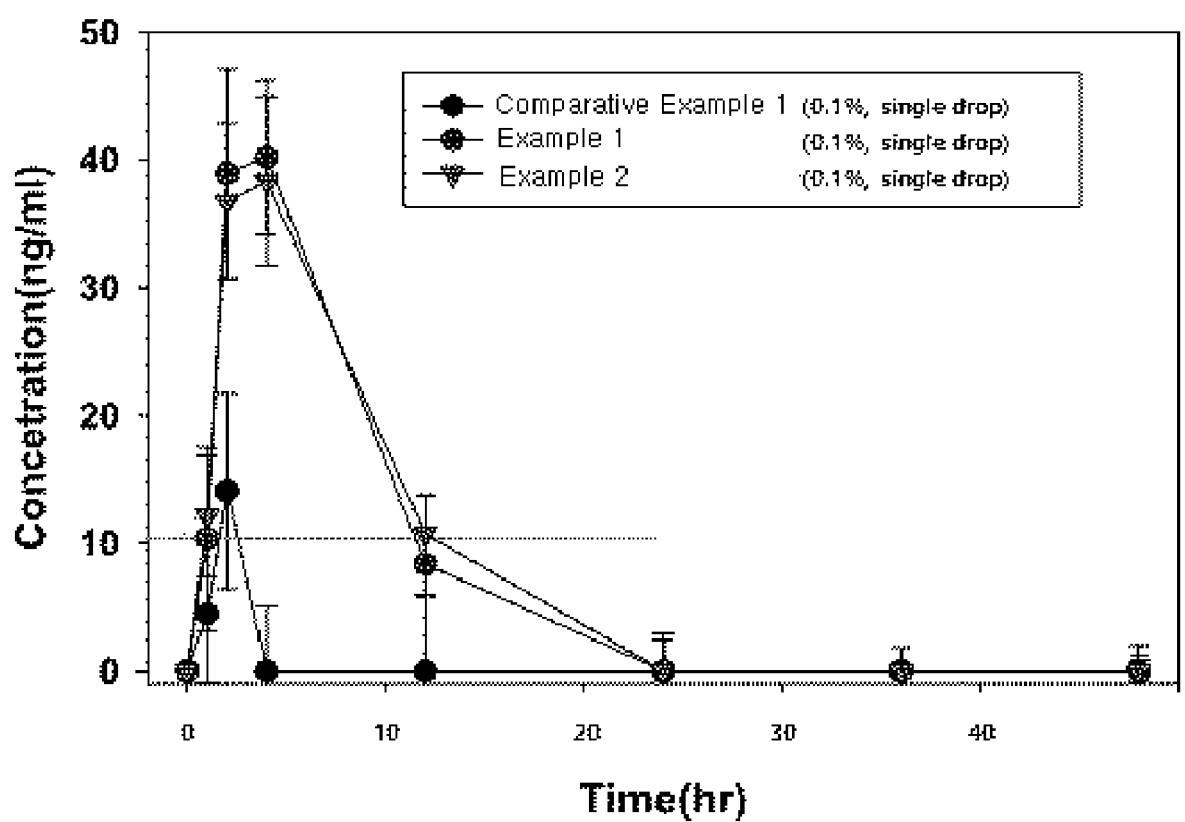
FIG. 7 is a graph showing drug release after administering carrier compositions of Examples 1 and 2 of the present disclosure and Comparative Example 1 to animals.

The results in Table 9 above are shown in FIG. 6, and the test results for Examples 1 and 3 and Comparative Example 1 are shown in FIG. 7.

[Test Results]

At 0.5, 1, 2, 6, 12, 18 and 24 hours after each of Examples 1 and 3 and Comparative Example 1, which contained dexamethasone sodium phosphate (DSP) as an active ingredient, was applied dropwise to both eyes of each rabbit, the change in the concentration of the DSP was analyzed.

As a result, it was confirmed that in the case of Examples 1 and 3, the DSP concentration was maintained up to about 24 hours. At this time, it was confirmed that the Cmax was 4 hours after the eye drop application, and the Tmax was 40.17 ng/ml. In the case of Comparative Example 1, the DSP concentration was maintained up to 4 hours. At this time, it was confirmed that the Cmax was 2 hours after the eye drop application, and the Tmax was 14.08 ng/ml.

These results show that the test substances of Examples 1 and 3 are maintained at a higher concentration in the aqueous humor compared to that of Comparative Example 1, and are long-lasting.

Test Example 5—Test for Evaluation of Pharmacological Effect

Using preclinical models secured by phacoemulsification and human intraocular lens implantation using New Zealand rabbits, a test was performed to examine the increases in anterior inflammatory cells and pro-inflammatory protein after intraocular lens implantation. Each of the anti-inflammatory eye drop compositions of Examples 1 and 3 and Maxidex (Alcon Inc. Switzerland; drug content: 1.0% (1 mg/mL)) as a reference example was administered.

Figure 8:
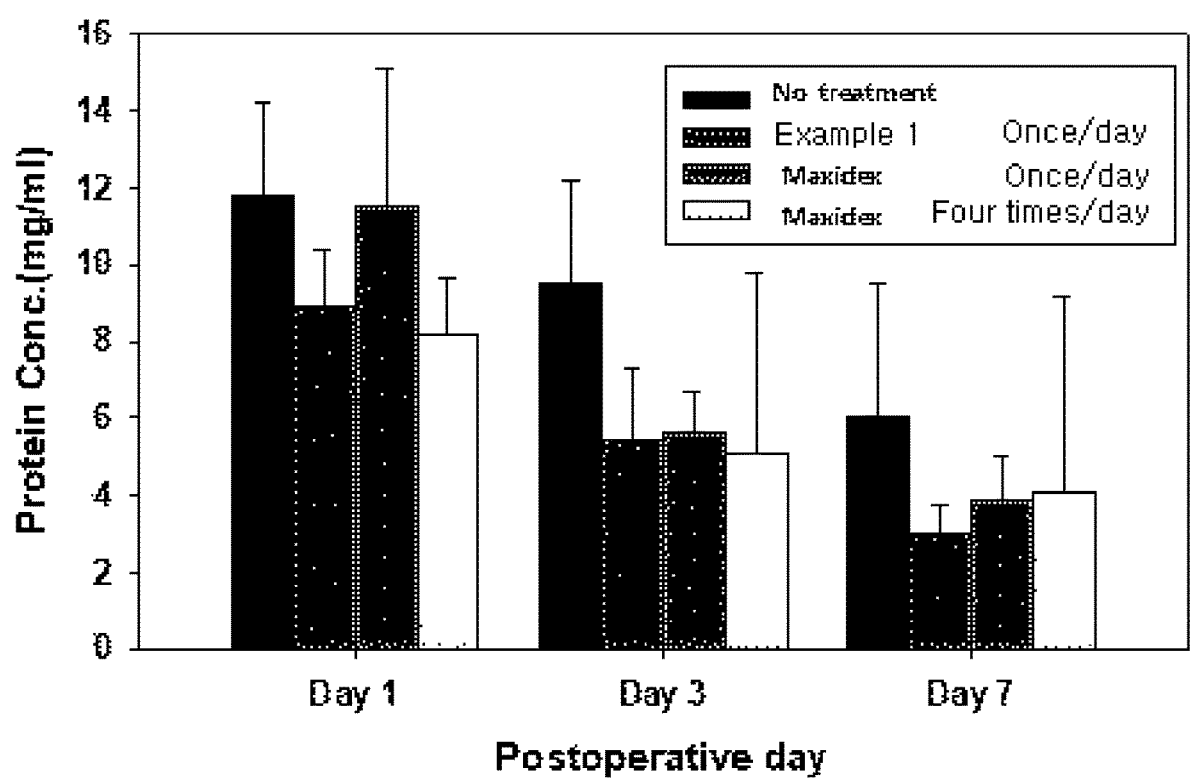
FIGS. 8 and 9 are graphs showing the concentration of pro-inflammatory protein (FIG. 8) and the counts of inflammatory cells (FIG. 9) after administering a pharmaceutical composition including the carrier composition according to the present disclosure to New Zealand rabbits.
Figure 9:
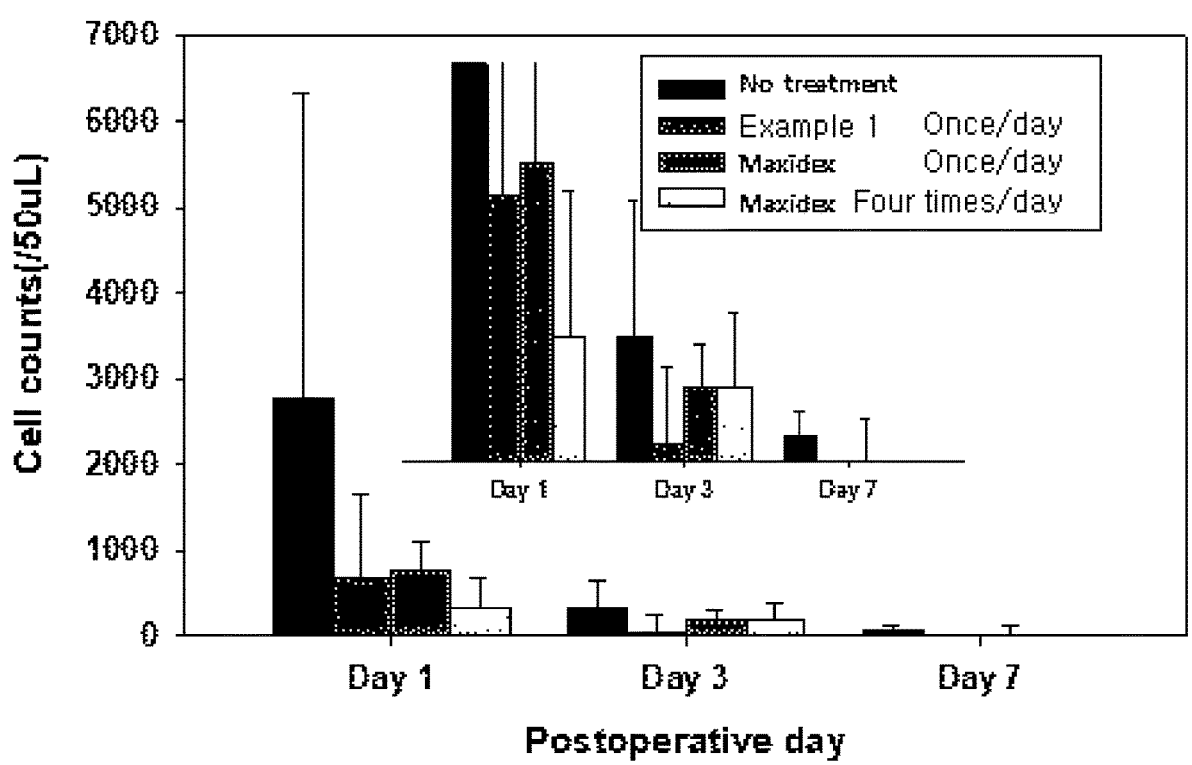

FIG. 8 shows the results of measuring the concentration of pro-inflammatory protein, and FIG. 9 shows the results of counting inflammatory cells.

Referring to FIGS. 8 and 9, it can be seen that even when the eye drop composition of Example 1 is administered once a day, it significantly reduces the concentration of pro-inflammatory protein and also significantly reduces the number of inflammatory cells.

It can be confirmed that the eye drop composition of Example 1 has a particularly excellent effect even compared to when Maxidex of the reference example, which contains the same amount of the drug, was administered four times a day. This is an effect obtained because the carrier composition of the Example sustainedly releases the drug, so that the efficacy of the drug is maintained for a long time even when applied dropwise to the eye once.

Test Example 6—Test for Comparative Evaluation of Pharmacological Effects

According to the same method as Test Example 5, a test was performed to evaluate the pharmacological effects of Examples 1 and 3, a negative control (saline), and a positive control (Maxidex).

Figure 10:
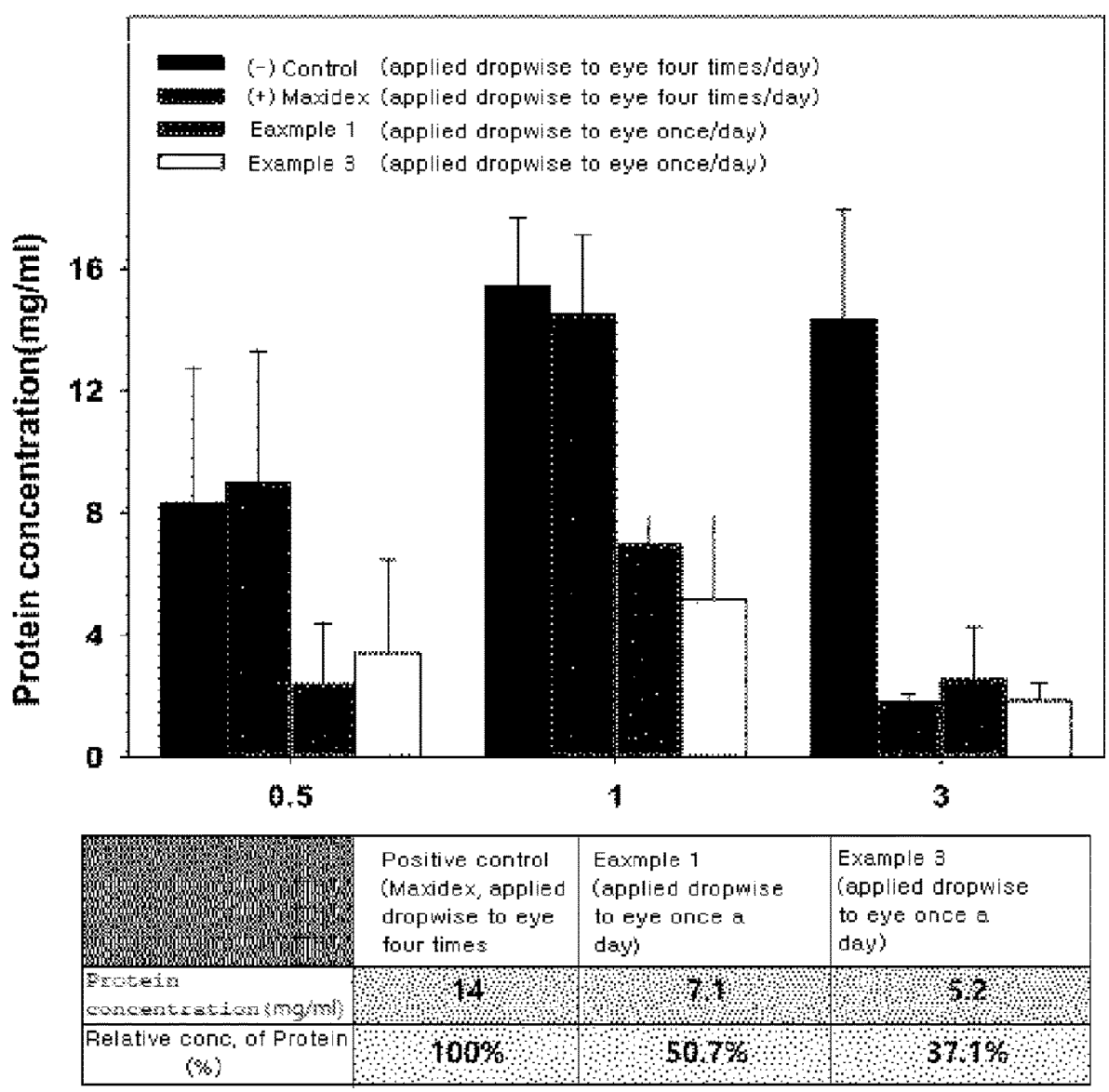
FIGS. 10 and 11 are graphs showing the concentration of pro-inflammatory protein (FIG. 10) and the counts of inflammatory cells (FIG. 11) after administering pharmaceutical compositions including carrier compositions of Examples 1 and 3 to New Zealand rabbits.
Figure 11:
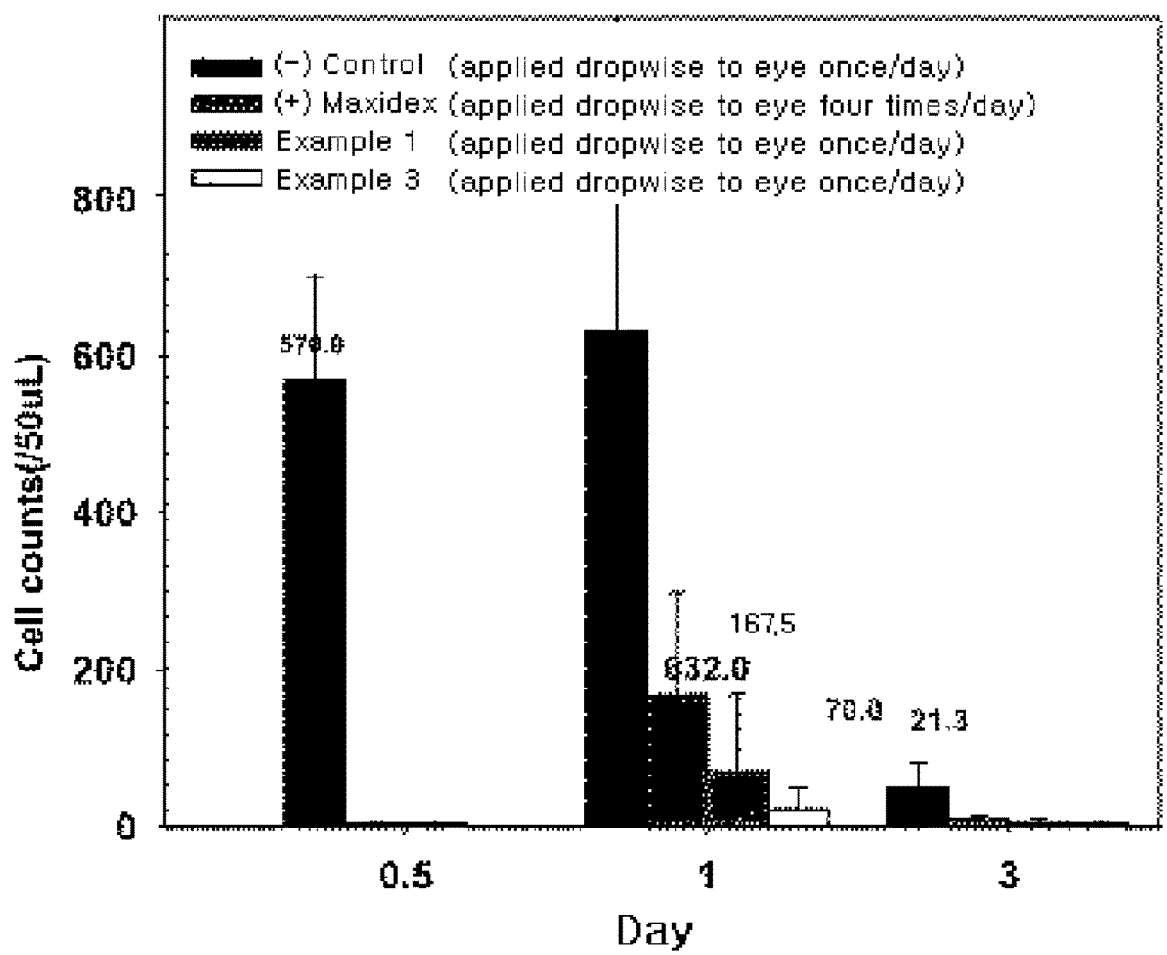

FIG. 10 shows the results of measuring the concentration of pro-inflammatory protein, and FIG. 11 shows the results of counting inflammatory cells.

Each of the negative and positive controls was applied dropwise to the eye four times a day, and each of Examples 1 and 3 was applied dropwise to the eye once a day. On days 0, 1 and 3, the aqueous humor was collected, and inflammatory cells and inflammation-related protein in the collected aqueous humor were analyzed. The results of the analysis are shown in FIGS. 10 and 11.

Referring to FIGS. 10 and 11, it can be confirmed that even when Examples 1 and 3 were administered once a day, they significantly inhibited inflammatory cells and significantly reduced the concentration of pro-inflammatory protein, compared to the positive control Maxidex administered four times a day according to the currently commercially available treatment method.

The invention claimed is:

1. A carrier composition for eye drops in which a substance to be delivered is loaded in a carrier,
    wherein the substance to be delivered comprises one or more selected from the group consisting of an anti-inflammatory agent, a glaucoma treatment agent, a calcium channel blocker (CCB), an NMDA-receptor blocker, an antioxidant, a nitric oxide synthase inhibitor, a heat shock protein (HSP), a cystinosis treatment agent, and an antibiotic,
    the carrier has a spherical shape,
    the carrier comprises a multilayer shell in a region ranging from the center to the surface of the carrier,
    the multilayer shell comprises a core located in the center of the carrier and comprising a carboxymethyl cellulose (CMC)-based hydrogel having a degree of substitution (D.S.) of 0.9, a first shell located on the surface of the core and comprising a CMC-based hydrogel having a degree of substitution of 0.8, a second shell located on the surface of the first shell and comprising a CMC-based hydrogel having a degree of substitution of 0.6, and a third shell located on the surface of the second shell and comprising a CMC-based hydrogel having a degree of substitution of 0.65, and
    the multilayer shell comprises the core having a radius equal to 25% of a radial length of the carrier, the first shell having a thickness equal to 20% of the radial length, the second shell having a thickness equal to 40% of the radial length, and the third shell having a thickness equal to 15% of the radial length.

2. The carrier composition of claim 1, wherein the anti-inflammatory agent comprises one or more selected from the group consisting of dexamethasone, diclofenac, ketorolac, rimexolone and difluprednate.

3. The carrier composition of claim 1, wherein the carrier composition has an average particle diameter (D50) of 1 to 500 nm.

4. The carrier composition of claim 1, wherein the carrier composition inhibits inflammation or infection after surgery for ophthalmic disease.

5. The carrier composition of claim 1, wherein the ophthalmic disease is cataract.

6. A pharmaceutical composition comprising: the carrier composition of claim 1; and an additive.

7. The pharmaceutical composition of claim 6, wherein the pharmaceutical composition is applied dropwise to an eye once a day.

8. A method for preparing the pharmaceutical composition according to claim 6, the method comprising a process of sterilizing the carrier composition with a filter, wherein an absolute value of content change between before and after the process of sterilizing the carrier composition with the filter is less than 1%.

\* \* \* \* \*